(12) United States Patent
Lee et al.

(10) Patent No.: US 8,940,762 B2
(45) Date of Patent: Jan. 27, 2015

(54) METHODS FOR TREATING PAIN

(75) Inventors: Chih-Hung Lee, Vernon Hills, IL (US); Michael R. Schrimpf, Grayslake, IL (US); Timothy A. Esbenshade, Schaumburg, IL (US); Chang Z. Zhu, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 586 days.

(21) Appl. No.: 12/975,526

(22) Filed: Dec. 22, 2010

(65) Prior Publication Data

US 2011/0178121 A1   Jul. 21, 2011

Related U.S. Application Data

(60) Provisional application No. 61/296,698, filed on Jan. 20, 2010.

(51) Int. Cl.
| | | |
|---|---|---|
| *A01N 43/42* | (2006.01) | |
| *A61K 31/44* | (2006.01) | |
| *C07D 451/02* | (2006.01) | |
| *C07D 451/00* | (2006.01) | |
| *A61K 31/46* | (2006.01) | |
| *A61K 31/55* | (2006.01) | |
| *A61K 45/06* | (2006.01) | |

(52) U.S. Cl.
CPC .................. *A61K 31/46* (2013.01); *A61K 31/55* (2013.01); *A61K 45/06* (2013.01)
USPC ............ 514/304; 514/299; 546/124; 546/127

(58) Field of Classification Search
USPC ............................ 514/304, 299; 546/124, 127
See application file for complete search history.

(56) References Cited

U.S. PATENT DOCUMENTS

| | | | |
|---|---|---|---|
| 2004/0002513 A1 | 1/2004 | Mazurov et al. | |
| 2004/0242641 A1 | 12/2004 | Buckley et al. | |
| 2008/0045539 A1 | 2/2008 | Ji et al. | |
| 2010/0093746 A1* | 4/2010 | Feuerbach et al. | 514/252.04 |

FOREIGN PATENT DOCUMENTS

| | | |
|---|---|---|
| WO | WO2007063071 A1 | 6/2007 |
| WO | WO2007137030 A2 | 11/2007 |

OTHER PUBLICATIONS

Gibofsky et al. Am. J. Ther., 2008, vol. 15, Issue 3, abstract.*
Becker, "A Short Synthesis of 1-Azaadamantan-4-One and the 4r and 4s Isomers of 4-Amino-1-Azaadamantane," Synthesis, 1992, vol. 11, pp. 1080-1082.
Bennett, et al., "A Peripheral Mononeuropathy in Rat that Produces Disorders of Pain Sensation like those Seen in Man," Pain, 1988, vol. 33 (1), pp. 87-107.
Bennett, et al. "Neuropathic Pain: New Insights, New Interventions, Hospital Practice," Hospital Practice, 1998, vol. 33 (10), pp. 95-114.
Bunnelle, et al., "Neuronal Nicotinic Acetylcholine Receptor Ligands as Potential Analgesics," Expert Opinion on Therapeutic Patents, 2003, vol. 13 (7), pp. 1003-1021.
Chandran, et al., "Pharmacological modulation of movement-evoked pain in a rat model of osteoarthritis", 2009, vol. 613, pp. 39-45.
Chaplan, et al., "Quantitative Assessment of Tactile Allodynia in the Rat Paw," Journal of Neuroscience Methods, 1994, vol. 53, pp. 55-63.
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
Damaj, et al., "The Antinociceptive Effects of α7 Nicotinic Agonists in an Acute Pain Model," Neuropharmacology, 2000, vol. 39 (3), pp. 2785-2791.
Decker, et al., "The Therapeutic Potential of Nicotinic Acetylcholine Receptor Agonists for Pain Control," Expert Opinion on Investigational Drugs, 2001, vol. 10 (10), pp. 1819-1830.
Dixon, "Efficient Analysis of Experimental Observations," Annual Review of Pharmacology and Toxicology, 1980, vol. 20, pp. 441-462.
Eliel, et al., "Stereochemistry of Organic Compounds," 1994, pp. 119-120, 1206, John Wiley & Sons, Inc. New York. Table of Contents.
Furniss, et al., Vogel's Textbook of Practical Organic Chemistry, 5th Edition, Longman Scientific & Technical, 1989, Table of Contents.
Higuchi, et al., "Bioreversible Carriers in Drug Design, A.C.S. Symposium Series," Pro-drugs as Novel Delivery Systems, 1987, vol. 14, Edward B. Roche, American Pharmaceutical Association and Pergamon Press. Table of Contents.
International Search Report and Written Opinion for Application No. PCT/US2010/061713, mailed on Apr. 27, 2011, 10 pages.
McQuay, et al., "Anticonvulsant drugs for management o pain: a systematic review," BMJ, vol. 311 (7012), pp. 1047-1052, 1995.
Medhurst, et al., "Activation of the $α_7$-Nicotinic Acetylcholine Receptor Reverses Complete Freund Adjuvant-Induced Mechanical Hyperalgesia in the Rat Via a Central Site of Action", 2008, vol. 9(7), pp. 580-587.
Poste, et al., "Lipid Vesicles as Carriers for Introducing Biologically Active Materials into Cells," Methods in Cell Biology, 1976, vol. 14, pp. 33-71.
Vincler, "Neuronal Nicotinic Receptors As Targets for Novel Analgesics," Expert Opinion on Investigational Drugs, 2005, vol. 14 (10), pp. 1191-1198.
Gibofsky, A. et al., "Chronic pain of osteoarthritis: considerations for selecting an extended-release opioid analgesic," Am. J. Therap. (2008) 15:241-255.

* cited by examiner

*Primary Examiner* — Samira Jean-Louis
(74) *Attorney, Agent, or Firm* — Nancy Gettel (57) ABSTRACT

The present invention is directed to methods of treating pain by administering a therapeutically effective amount of an α7 nAChR ligand or a pharmaceutically acceptable salt thereof, to a mammal in need of treatment thereof and to pharmaceutical compositions comprising such a compound or salt.

4 Claims, 2 Drawing Sheets

METHODS FOR TREATING PAIN

CROSS-REFERENCE TO RELATED APPLICATIONS

This patent application claims priority to U.S. Provisional Patent Application No. 61/296,698, filed on Jan. 20, 2010, the entirety of which is incorporated herein by reference.

BACKGROUND OF THE INVENTION

1. Technical Field

The invention relates to methods for treating pain, including nociceptive and/or neuropathic pain, and compositions useful in the treatment of pain and pain related conditions. In particular, the methods of the present invention relates to the use of a neuronal nicotinic acetylcholine receptor ligand of formula (I), a pharmaceutically acceptable salt thereof or a composition comprising such compound or salt to treat pain in a subject in need of treatment thereof.

2. Description of Related Technology

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. Nociceptive pain can be experienced as sharp, dull, or aching. This pain and tenderness are considered "acute" nociceptive pain. This pain and tenderness gradually diminish as healing progresses and disappear when healing is complete. Examples of acute nociceptive pain include surgical procedures (post-op pain), burns, ocular pain, inflammation (due to infection or arthritis) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain may refer to peripheral neuropathic pain, which is caused by damage to nerves, or to central neuropathic pain, which is caused by damage to the brain, brainstem, or spinal cord. Neuropathic pain is not associated with nociceptive stimulation, although the passage of nerve impulses that is ultimately perceived as pain by the brain is the same in both nociceptive and neuropathic pain. Neuropathic pain is extremely difficult to manage; it is usually chronic and fails to respond to standard analgesic interventions. Administration of morphine may give some degree of relief but at doses that are impractical for lifelong treatments (Bennett, Hosp. Practice Vol. 33, pages 95 to 114, 1998). The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including fibromyalgia, trigeminal neuralgia, post-herpetic neuralgia, traumatic neuralgia, phantom limb, headaches, as well as a number of other disorders of ill-defined or unknown origin.

Current analgesics fall into two classes, nonsteroidal anti-inflammatory drugs (NSAIDs) and opioids. NSAIDs are effective for mild to moderate pain with an inflammatory component but are not particularly effective in severe or in chronic neuropathic pain. Further, the use of NSAIDs has been limited by their gastrointestinal side effects. Opioids, such as morphine, are effective in severe acute pain but provide only limited relief in neuropathic pain. In addition, opioids are controlled substances and are limited in their application due to a wide range of side effects including constipation, nausea, cognitive impairment and tolerance issues.

Tricyclic antidepressants and anticonvulsants are also used in the treatment of various pain states, including neuropathic pain. Such drugs typically target the serotonergic and noradrenergic systems and increase the available extracellular levels of both serotonin and norepinephrine. It has been proposed that the postsynaptic activation of $\alpha 2$-adrenoceptors by norepinephrine may be the mechanism through which these compounds alleviate neuropathic pain. However, since antidepressants readily cross the blood-brain barrier, their ability to increase the levels of serotonin and norepinephrine may cause the undesired activation of other receptors leading to the high risk of centrally-mediated side effects. Side effects of antidepressants range from mild but irritating symptoms such as dry mouth and sedation to severe life threatening side effects such as postural hypotension and cardiac arrhythmias. The effectiveness of anticonvulsants in the treatment of various pain states, including neuropathic pain, has also been evaluated (McQuay et al. (1995) Anticonvulsant Drugs For The Management of Pain: A Systematic Review, *British Medical Journal* 311, 1047-52). Similar to antidepressants, side effects frequently occur with these medications.

Neuronal nicotinic receptors have been targeted for pain and various other central nervous system diseases. See, for example, Vincler, M., Neuronal nicotinic receptors as targets for novel analgesics, *Exp. Opin. Invest. Drugs,* 2005, 14 (10): 1191-1198; Bunnelle, W. H., Decker, M. W., Neuronal nicotinic acetylcholine receptor ligands as potential analgesics, *Exp. Opin. Ther. Patents,* 2003, 13 (7): 1003-1021; Decker, M. W., Meyer, M. D., Sullivan, J. P., The therapeutic potential of nicotinic acetylcholine receptor agonists for pain control, *Exp. Opin. Invest. Drugs,* 2001, 10 (10): 1819-1830. Evidence for analgesic efficacy was first demonstrated by the partial inhibition of nicotine-induced anti-nociception with the $\alpha 7$ antagonists methyllycaconitine (MLA) and $\alpha$-bungarotoxin. More recently, efficacy for selective $\alpha 7$ agonists has been established in rodent models of peripheral nerve injury. (Damaj, M. Imad et. al., The antinociceptive effects of $\alpha 7$ nicotinic agonists in an acute pain model, *Neurophamacology* (2000), 39, 2785-2791). The analgesic efficacy of $\alpha 7$ receptor agonists in inflammatory pain models has also been investigated. (Medhurst, S., et al., Activation of the $\alpha 7$-Nicotinic Acetylcholine Receptor Reverses Complete Freund Adjuvant-Induced Mechanical Hyperalgesia in the Rat Via a Central Site of Action. *Journal of Pain* (2008), 9(7), 580-587.)

Pain is an unmet medical need and the methods and possibilities for treatments of such indications are insufficient. In light of the significance of acute and chronic pain in the lives of many patients, and the limitations in their treatment, it would be beneficial to identify new compositions and methods of treating such disorders, particularly in a manner that reduces adverse ganglionic effects such as at the gastrointestinal systems (e.g. nausea and emesis).

SUMMARY OF THE INVENTION

The present invention relates to methods of treating, controlling or preventing pain in a patient in need of treatment thereof comprising administering a therapeutically effective amount of an α7 nAChR ligand, such as those compounds having the formula (I):

(I)

or a pharmaceutically acceptable salt, solvate, ester, amide or prodrug thereof, wherein n is 1, 2 or 3;
A is N or N$^+$—O$^-$;
R is hydrogen, alkyl, cycloalkylalkyl and arylalkyl;
L is selected from the group consisting of O, S, and —N(R$_a$)—;
Ar$^1$ is a 6-membered aryl or 6 membered heteroaryl ring;
Ar$^2$ is a bicyclic heteroaryl; and
R$_a$ is selected from the group consisting of hydrogen, alkyl and alkylcarbonyl; provided that if Ar$^1$ is then L is O or S.

In one aspect of the present invention, the method includes, at least in part, administering a therapeutically effective amount of a compound of formula (I), or a pharmaceutically acceptable salt, solvate, ester, amide or prodrug thereof to a mammal in need of such treatment.

The methods of the present invention can be used to treat any type of acute or chronic pain condition or disorder, including nociceptive pain, neuropathic pain or a combination thereof. Such pain conditions or disorders can include, but are not limited to, post-operative pain, osteoarthritis pain, pain due to inflammation, rheumatoid arthritis pain, musculoskeletal pain, burn pain (including sunburn), ocular pain, the pain associated with dental conditions (such as dental caries and gingivitis), post-partum pain, bone fracture, herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, hyperalgesia and cancer.

In certain other embodiments, the present invention is a method of treating osteoarthritic pain in a subject in need of such treatment by administering a therapeutically effective amount of a compound of formula (I), or a pharmaceutically acceptable salt, solvate, ester, amide or prodrug thereof or a composition comprising a compound of formula (I), or a pharmaceutically acceptable salt, solvate, ester, amide or prodrug thereof to the subject.

Accordingly, the present invention is directed to use of a compound of formula (I) or compositions comprising a compound of formula (I), or a pharmaceutically acceptable salt, solvate, ester, amide or prodrug thereof in the prevention, alleviation and/or management of pain, pain conditions, pain related disorders and inflammation as described herein.

In other embodiments, the methods of the present invention comprise use of a compound of formula (I) or a pharmaceutically acceptable salt, solvate, ester, amide or prodrug thereof for selectively modulating nAChR activity, for example, α7 nAChR activity, to treat, prevent and/or alleviate a pain condition, pain disorder or inflammation related to α7 nAChR activity in mammals. The invention also provides compositions for the treatment of subjects with nAChR-mediated diseases or disorders, and particularly for pain, which include a compound of formula (I) or a pharmaceutically acceptable salt, solvate, ester, amide or prodrug thereof.

In certain embodiments, the methods of the present invention comprise administering to the mammal a therapeutically effective amount of a compound of formula (I) or a pharmaceutically acceptable salt, solvate, ester, amide or prodrug thereof, in combination with one or more analgesics (for example, acetaminophen or opioids such as, but not limited to, morphine), or with one or more nonsteroidal anti-inflammatory drug (NSAID); or administered with a combination of one or more analgesics and one or more NSAID. Examples of suitable NSAIDs include, but are not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. In certain embodiments, the composition may optionally include one or more pharmaceutically acceptable carriers.

The methods of the present invention can further include administering to the mammal a therapeutically effective amount of a compound of formula (I) or a pharmaceutically acceptable salt, solvate, ester, amide or prodrug thereof, in combination with one or more tricyclic antidepressants such as amitriptyline, desipramine, doxepin, imipramine and nortriptyline. Other embodiments of the present invention can include administering to the mammal a therapeutically effective amount of a compound of formula (I) or a pharmaceutically acceptable salt, solvate, ester, amide or prodrug thereof, in combination with one or more anticonvulsant, such as pregabalin, carbamazepine, gabapentin, lamotrigine, oxcarbazepine, tiagabine and topiramate. In certain other embodiments of the present invention, the methods can include administering to the mammal a therapeutically effective amount of a compound of formula (I) or a pharmaceutically acceptable salt, solvate, ester, amide or prodrug thereof, in combination with a therapeutic agent such as a nicotinic acetylcholine receptor subtype α7 positive allosteric modulator.

Accordingly, the present invention provides pharmaceutical compositions comprising a compound of formula (I), or a pharmaceutically acceptable salt, solvate, ester, amide or prodrug thereof for use in the treatment of pain, in combination with one or more pharmaceutically acceptable carriers or diluents. Further embodiments of the present invention include pharmaceutical compositions comprising a compound of formula (I), or a pharmaceutically acceptable salt, solvate, ester, amide or prodrug thereof in combination with one or more analgesic agent, opioid, NSAID, anticonvulsant and/or therapeutic agent, as described herein.

These embodiments and further embodiments are contemplated as part of the invention, as further described herein.

BRIEF DESCRIPTION OF THE DRAWINGS

The following is a description of the figures which are presented for the purposes of illustrating the invention and not for purposes of limiting the same.

DETAILED DESCRIPTION OF THE INVENTION

The present invention is directed to methods of treating, controlling or preventing pain in a patient in need of treatment thereof using an α7 nAChR ligand. In particular, the present invention provides methods for treating or preventing pain using α7 nAChR ligands, such as the compounds of formula (I), as recited above. The method can include, at least in part, administering a therapeutically effective amount of a compound of formula (I), or a pharmaceutically acceptable salt, solvate, ester, amide or prodrug thereof to a patient in need of treatment. Compounds of formula (I), salts and methods of preparing them are described in U.S. Patent Publication No. 2008/0045539, published Feb. 21, 2008, which is hereby incorporated by reference in its entirety.

Compounds of formula (I) particularly useful in the methods of the present invention are those wherein $Ar^1$ is selected from, but is not limited to:

wherein $R_1$, $R_2$, $R_3$, $R_4$ and $R_5$ are independently acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —$NR_gR_j$, $(NR_gR_j)$alkyl, $(NR_gR_j)$alkoxy, $(NR_gR_j)$carbonyl, or $(NR_gR_j)$sulfonyl; $R_g$ and $R_j$ are each independently hydrogen or alkyl.

Further, in certain embodiments of the present invention, compounds of formula (I) for use in the present invention can include, but are not limited to, those wherein $Ar^2$ is selected from:

(i)

(ii)

(iii)

(iv)

(v)

(vi)

(vii)

(viii)

(ix)

(x)

and

-continued (xi)

wherein $Z_1$, $Z_2$, $Z_3$ and $Z_4$ are each independently nitrogen or are carbon, wherein the carbon atom is optionally substituted with a substituent selected from the group consisting of hydrogen, halogen, alkyl, —$OR_c$, -alkyl-$OR_c$, —$NR_dR_e$, and -alkyl-$NR_dR_e$; $R_b$ is selected from the group consisting of hydrogen, alkyl and alkylcarbonyl; $R_c$ is alkyl; $R_d$ and $R_e$ are each independently selected from the group consisting of hydrogen and alkyl, $R_6$ and $R_7$ are each independently selected from the group consisting of hydrogen, alkenyl, alkoxy, alkoxyalkoxy, alkoxyalkyl, alkoxycarbonyl, alkoxyimino, alkoxysulfonyl, alkyl, alkylcarbonyl, alkylcarbonyloxy, alkylsulfonyl, alkynyl, carboxy, cyano, formyl, haloalkoxy, haloalkyl, halo, hydrogen, hydroxy, hydroxyalkyl, mercapto, nitro, thioalkoxy, —$NR_gR_j$, $(NR_gR_j)$alkyl, $(NR_gR_j)$alkoxy, $(NR_gR_j)$carbonyl, and $(NR_gR_j)$sulfonyl; $R_g$ and $R_j$ are each independently selected from the group consisting of hydrogen and alkyl.

R is selected from hydrogen, alkyl, cycloalkylalkyl, and arylalky. Preferred compounds are disclosed wherein R is hydrogen and alkyl. Preferably, R is methyl and hydrogen.

Preferred compounds of formula (I) for use in the present invention can include those compounds wherein $Ar^2$ is (i)

(iv)

(ix)

Particularly, the invention relates to methods of treating, preventing or controlling pain using compounds of formula (I) wherein A is N; R is selected from methyl and hydrogen; L is O; n is 2; and $Ar^2$ is selected from the group of consisting of:

(i)

(iv)

and (ix)

More particularly, the invention relates to compounds of formula (I) wherein A is N; R is methyl or hydrogen; L is O; n is 2; $Ar^1$ is and
$Ar^2$ is (i)

The methods of the invention utilize compounds of formula (I) including but not limited to those specified in the examples or otherwise specifically named, that can modulate, and often possess an affinity for, nAChRs, and more particularly α7 nAChRs. It has been shown that such compounds can be useful for the treatment or prevention of a number of acute or chronic pain conditions or disorders, including nociceptive pain, neuropathic pain or a combination thereof. Such pain conditions or disorders can include, but are not limited to, post-operative pain, osteoarthritis pain, pain due to inflammation, rheumatoid arthritis pain, musculoskeletal pain, burn pain (including sunburn), ocular pain, the pain associated with dental conditions (such as dental caries and gingivitis), post-partum pain, bone fracture, herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, hyperalgesia and cancer.

Specific examples of compounds that can be useful in the methods of the present invention include, but are not limited to, compounds such as:

5-{6-[(endo)-8-methyl-8-aza-bicyclo[3.2.1]oct-3-yloxy]-pyridazin-3-yl}-1H-indole;

(endo)-3-(6-benzo[b]thiophen-5-yl-pyridazin-3-yloxy)-8-methyl-8-aza-bicyclo[3.2.1]octane;
(endo)-3-[6-(benzofuran-5-yl)-pyridazin-3-yloxy]-8-methyl-8-aza-bicyclo[3.2.1]octane;
6-{6-[(endo)-8-methyl-8-aza-bicyclo[3.2.1]oct-3-yloxy]-pyridazin-3-yl}-1H-indole;
5-{6-[(endo)-8-methyl-8-aza-bicyclo[3.2.1]oct-3-yloxy]-pyridazin-3-yl}-1H-indazole;
1-methyl-5-{6-[(endo)-8-methyl-8-aza-bicyclo[3.2.1]oct-3-yloxy]-pyridazin-3-yl}-1H-indole;
5-{6-[(endo)-8-methyl-8-aza-bicyclo[3.2.1]oct-3-yloxy]-pyridazin-3-yl}-2-trifluoromethyl-1H-indole;
5-{6-[(exo)-8-methyl-8-aza-bicyclo[3.2.1]oct-3-yloxy]-pyridazin-3-yl}-1H-indole;
5-{5-[(endo)-8-methyl-8-aza-bicyclo[3.2.1]oct-3-yloxy]-pyridin-2-yl}-1H-indole;
(endo)-3-(6-benzo[b]thiophen-5-yl-pyridin-3-yloxy)-8-methyl-8-aza-bicyclo[3.2.1]octane;
5-{5-[(exo)-8-methyl-8-aza-bicyclo[3.2.1]oct-3-yloxy]-pyridin-2-yl}-1H-indole;
(exo)-3-[6-(benzofuran-5-yl)-pyridin-3-yloxy]-8-methyl-8-aza-bicyclo[3.2.1]octane;
5-{5-[(exo)-8-methyl-8-aza-bicyclo[3.2.1]oct-3-yloxy]-pyridin-2-yl}-1H-indazole;
5-{5-[(exo)-8-methyl-8-aza-bicyclo[3.2.1]oct-3-yloxy]-pyridin-2-yl}-2-trifluoromethyl-1H-indole;
4-{5-[(exo)-8-methyl-8-aza-bicyclo[3.2.1]oct-3-yloxy]-pyridin-2-yl}-1H-indole;
5-{6-[(endo)-8-methyl-8-aza-bicyclo[3.2.1]oct-3-yloxy]-pyridin-3-yl}-1H-indole;
(endo)-3-(5-benzo[b]thiophen-5-yl-pyridin-2-yloxy)-8-methyl-8-aza-bicyclo[3.2.1]octane;
5-{6-[(exo)-8-methyl-8-aza-bicyclo[3.2.1]oct-3-yloxy]-pyridin-3-yl}-1H-indole;
[6-(1H-indol-5-yl)-pyridin-3-yl]-[(endo)-8-methyl-8-azabicyclo[3.2.1]oct-3-yl]-amine;
[6-(benzofuran-5-yl)-pyridin-3-yl]-[(endo)-8-methyl-8-azabicyclo[3.2.1]oct-3-yl]-amine;
[(endo)-8-methyl-8-aza-bicyclo[3.2.1]oct-3-yl]-[6-(2-trifluoromethyl-1H-indol-5-yl)-pyridin-3-yl]-amine;
[6-(1H-indazol-5-yl)-pyridin-3-yl]-[(endo)-8-methyl-8-azabicyclo[3.2.1]oct-3-yl]-amine;
[6-(1H-indol-4-yl)-pyridin-3-yl]-[(endo)-8-methyl-8-azabicyclo[3.2.1]oct-3-yl]-amine;
[(endo)-8-aza-bicyclo[3.2.1]oct-3-yl]-[6-(1H-indol-5-yl)-pyridin-3-yl]-amine;
[4-(1H-indol-5-yl)-phenyl]-[(endo)-8-methyl-8-aza-bicyclo[3.2.1]oct-3-yl]-amine;
[4-(1H-indazol-5-yl)-phenyl]-[(endo)-8-methyl-8-aza-bicyclo[3.2.1]oct-3-yl]-amine;
[(endo)-8-methyl-8-aza-bicyclo[3.2.1]oct-3-yl]-[4-(1-methyl-1H-indol-5-yl)-phenyl]-amine;
(4-benzo[b]thiophen-5-yl-phenyl)-[(endo)-8-methyl-8-azabicyclo[3.2.1]oct-3-yl]-amine;
[4-(benzofuran-5-yl)-phenyl]-[(endo)-8-methyl-8-aza-bicyclo[3.2.1]oct-3-yl]-amine;
[4-(1H-indol-4-yl)-phenyl]-[(endo)-8-methyl-8-aza-bicyclo[3.2.1]oct-3-yl]-amine;
[3-(1H-indol-5-yl)-phenyl]-[(endo)-8-methyl-8-aza-bicyclo[3.2.1]oct-3-yl]-amine;
[3-(1H-indol-4-yl)-phenyl]-[(endo)-8-methyl-8-aza-bicyclo[3.2.1]oct-3-yl]-amine;
5-{6-[(endo)-8-methyl-8-aza-bicyclo[3.2.1]oct-3-yloxy]-pyridazin-3-yl}-2-trifluoromethyl-1H-indole;
4-{6-[(exo)-8-methyl-8-aza-bicyclo[3.2.1]oct-3-yloxy]-pyridazin-3-yl}-1H-indole;
5-{6-[(exo)-8-methyl-8-aza-bicyclo[3.2.1]oct-3-yloxy]-pyridin-3-yl}-1H-indole;
5-{6-[(exo)-8-methyl-8-aza-bicyclo[3.2.1]oct-3-yloxy]-pyridin-3-yl}-2-trifluoromethyl-1H-indole;
4-{6-[(exo)-8-methyl-8-aza-bicyclo[3.2.1]oct-3-yloxy]-pyridazin-3-yl}-1H-indole;
6-{5-[(exo)-8-methyl-8-aza-bicyclo[3.2.1]oct-3-yloxy]-pyridin-2-yl}-1H-indole;
5-{5-[(endo)-8-methyl-8-aza-bicyclo[3.2.1]oct-3-yloxy]-pyrazin-2-yl}-1H-indole;
4-{5-[(endo)-8-methyl-8-aza-bicyclo[3.2.1]oct-3-yloxy]-pyrazin-2-yl}-1H-indole;
6-{5-[(endo)-8-methyl-8-aza-bicyclo[3.2.1]oct-3-yloxy]-pyrazin-2-yl}-1H-indole;
[6-(1H-indol-6-yl)-pyridin-3-yl]-[(endo)-8-methyl-8-azabicyclo[3.2.1]oct-3-yl]-amine;
5-{6-[(endo)-9-methyl-9-azabicyclo[3.3.1]nonan-3-yloxy]pyridazin-3-yl}-1H-indole;
(endo)-3-[6-(benzo[b]thiophen-5-yl)pyridazin-3-yloxy]-9-methyl-9-azabicyclo[3.3.1]nonane;
5-{5-[(endo)-8-methyl-8-aza-bicyclo[3.2.1]oct-3-yloxy]-pyrazin-2-yl}-1H-pyrrolo[2,3-b]pyridine;
5-{5-[(exo)-8-methyl-8-aza-bicyclo[3.2.1]oct-3-yloxy]-pyridin-2-yl}-1H-pyrrolo[2,3-b]pyridine;
5-{5-[(exo)-8-methyl-8-aza-bicyclo[3.2.1]oct-3-yloxy]-pyridin-3-yl}-1H-indole;
5-{5-[(exo)-8-methyl-8-aza-bicyclo[3.2.1]oct-3-yloxy]-pyrazin-2-yl}-1H-indole;
4-{5-[(exo)-8-methyl-8-aza-bicyclo[3.2.1]oct-3-yloxy]-pyrazin-2-yl}-1H-indole;
6-{5-[(exo)-8-methyl-8-aza-bicyclo[3.2.1]oct-3-yloxy]-pyrazin-2-yl}-1H-indole;
(endo)-N-(5-(1H-Indol-5-yl)pyridin-3-yl)-8-methyl-8-azabicyclo[3.2.1]octan-3-amine;
(endo)-N-(5-(1H-Indol-4-yl)pyridin-3-yl)-8-methyl-8-azabicyclo[3.2.1]octan-3-amine;
(endo)-N-(5-(1H-Indol-6-yl)pyridin-3-yl)-8-methyl-8-azabicyclo[3.2.1]octan-3-amine;
(endo)-N-{5-[2-(trifluoromethyl)-1H-indol-5-yl]pyridin-3-yl}-8-Methyl-8-azabicyclo[3.2.1]octan-3-amine;
5-{5-[(endo)-8-Methyl-8-azabicyclo[3.2.1]octan-3-yloxy]pyridin-2-yl}-1H-pyrrolo[2,3-b]pyridine;
5-{5-[(endo)-8-Methyl-8-azabicyclo[3.2.1]octan-3-yloxy]pyridin-2-yl}indolin-2-one;
5-{5-[(endo)-8-Azabicyclo[3.2.1]octan-3-yloxy]pyridin-2-yl}-1H-indole;
(1R,3r,5S,8s)-3-(6-(1H-Indol-5-yl)pyridin-3-yloxy)-8-methyl-8-azabicyclo[3.2.1]octane 8-oxide;
(1R,3r, 5S,8r)-3-(6-(1H-Indol-5-yl)pyridin-3-yloxy)-8-methyl-8-azabicyclo[3.2.1]octane 8-oxide;
4-{5-[(endo)-8-Azabicyclo[3.2.1]octan-3-yloxy]pyridin-2-yl}-1H-indole;
5-{5-[(exo)-8-Azabicyclo[3.2.1]octan-3-yloxy]pyridin-2-yl}-1H-indole;
5-{5-[(endo)-8-Azabicyclo[3.2.1]octan-3-yloxy]pyridin-2-yl}indolin-2-one;
5-{5-[(endo)-8-Azabicyclo[3.2.1]octan-3-yloxy]pyridin-2-yl}-1H-pyrrolo[2,3-b]pyridine;
5-{5-[(exo)-8-Azabicyclo[3.2.1]octan-3-yloxy]pyridin-2-yl}-1H-pyrrolo[2,3-b]pyridine,
or pharmaceutically acceptable salts, esters, amides, and prodrugs thereof.

Compound names are assigned by using AutoNom naming software, which is provided by MDL Information Systems GmbH (formerly known as Beilstein Informationssysteme) of Frankfurt, Germany, and is part of the CHEMDRAW® ULTRA v. 6.0.2 software suite.

Compounds of formula (I) may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30.

The attachment of L to the azabicyclic alkane may be considered to encompass both the endo and exo geometries, such as isomer (Ia) and (Ib). The configurational assignment of structures of formula (Ia) are assigned endo in accordance with that described in Stereochemistry of Organic Compounds, E. L. Eliel, S. H Wilen; John Wiley and Sons, Inc. 1994. Structures of formula (Ib) are assigned exo using the same methods.

The $N^+$—$O^-$ portion of isomer (Ic) and isomer (Id) are diastereomers. The configurational assignment of structures of formula (Ic) are assigned (r) in accordance with that described in Synthesis, 1992, 1080, Becker, D. P.; Flynn, D. L. and as defined in Stereochemistry of Organic Compounds, E. L. Eliel, S. H Wilen; John Wiley and Sons, Inc. 1994. In addition the configurational assignment of structures of formula (Id) are assigned (s) using the same methods.

The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

DEFINITION OF TERMS

Certain terms as used in the specification are intended to refer to the following definitions, as detailed below.

The term "acyl", as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy", as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl", as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy", as used herein, means an alkyl group as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy", as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl", as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl", as used herein, means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxyimino", as used herein, means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl", as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl", as used herein, means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl", as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio", as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl", as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido", as used herein, means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl", as used herein, means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —$NR_gR_j$, ($NR_gR_j$)alkyl, ($NR_gR_j$)alkoxy, ($NR_gR_j$)carbonyl, and ($NR_gR_j$)sulfonyl, wherein $R_g$ and $R_j$ are each independently selected from the group consisting of hydrogen and alkyl.

The term "arylcarbonyl", as used herein, means an aryl group, as defined herein, or a benzyl group appended to the parent molecular moiety through a carbonyl group, represented by —C(O)—, as defined herein. Representative examples of arylcarbonyl include, but are not limited to, phenylcarbonyl and benzylcarbonyl.

The term "aryloxycarbonyl", as used herein, means an aryl-O— group, wherein the aryl of aryl-O— is as defined herein, or a benzoxyl group appended to the parent molecular moiety through a carbonyl group, represented by —C(O)—, as defined herein. Representative examples of aryloxycarbonyl include, but are not limited to, phenoxycarbonyl and benzyloxycarbonyl.

The term "arylsulfonyl", as used herein, means an aryl group, as defined herein, appended to the parent molecular moiety through a sulfonyl group, as defined herein. Representative examples of arylsulfonyl include, but are not limited to, phenylsulfonyl, (methylaminophenyl)sulfonyl, (dimethylaminophenyl)sulfonyl, and (naphthyl)sulfonyl.

The term "carbonyl", as used herein, means a —C(O)— group.

The term "carboxy", as used herein, means a —$CO_2H$ group.

The term "cyano", as used herein, means a —CN group.

The term "formyl", as used herein, means a —C(O)H group.

The term "halo" or "halogen", as used herein, means —Cl, —Br, —I or —F.

The term "haloalkoxy", as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl", as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl" means an aromatic five- or six-membered ring containing 1, 2, 3, or 4 heteroatoms independently selected from group consisting of nitrogen, oxygen and sulfur. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridinyl, pyrimidinyl, pyrrolyl, tetrazolyl, thiadiazolyl, thiazolyl, thienyl, triazinyl, and triazolyl.

The heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —$NR_gR_j$, ($NR_gR_j$)alkyl, ($NR_gR_j$)alkoxy, ($NR_gR_j$)carbonyl, and ($NR_gR_j$)sulfonyl, wherein $R_g$ and $R_j$ are each independently selected from the group consisting of hydrogen and alkyl.

The term "bicyclic heteroaryl" refers to fused aromatic nine- and ten-membered bicyclic rings containing 1, 2, 3, or 4 heteroatoms independently selected from the group consisting of nitrogen, oxygen and sulfur. The bicyclic heteroaryl groups are connected to the parent molecular moiety through a carbon or nitrogen atom. Representative examples of bicyclic heteroaryl rings include, but are not limited to, unduly, indolyl, indazolyl, benzothiazolyl, benzofuranyl, isoquinolinyl, and quinolinyl. Bicyclic heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —$NR_gR_j$, ($NR_gR_j$)alkyl, ($NR_gR_j$)alkoxy, ($NR_gR_j$)carbonyl, and ($NR_gR_j$)sulfonyl, wherein $R_g$ and $R_j$ are each independently selected from the group consisting of hydrogen and alkyl.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of nitrogen, oxygen and sulfur. The 3 or 4 membered ring contains 1 heteroatom selected from the group consisting of nitrogen, oxygen and sulfur. The 5 membered ring contains zero or one double bond and one, two or three heteroatoms selected from the group consisting of nitrogen, oxygen and sulfur. The 6 or 7 membered ring contains zero, one or two double bonds and one, two or three heteroatoms selected from the group consisting of nitrogen, oxygen and sulfur. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle that is either fused to a cycloalkyl ring, a heteroaryl ring or another heterocyclic ring, or is formed by an alkyl chain attached to two non-adjacent carbons contained within the monocyclic heterocyclic ring. The bicyclic heterocycle is connected to the parent molecular moiety through any carbon atom or any nitrogen atom contained within the monocyclic heterocycle. Representative examples of bicyclic heterocycle include, but are not limited to, azabicyclo[3.1.1]heptane, azabicyclo[3.2.1]octane, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The heterocyclic groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —$NR_gR_j$, ($NR_gR_j$)alkyl, ($NR_gR_j$)alkoxy, ($NR_gR_j$)carbonyl, and ($NR_gR_j$)sulfonyl, wherein $R_g$ and $R_j$ are each independently selected from the group consisting of hydrogen and alkyl.

The term "hydroxy", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto", as used herein, means a —SH group.

The term "nitro", as used herein, means a —$NO_2$ group.

The term "—$NR_gR_j$", as used herein, means two groups, $R_g$ and $R_j$, which are appended to the parent molecular moiety through a nitrogen atom. $R_g$ and $R_j$ are each independently hydrogen or alkyl. Representative examples of —$NR_gR_j$ include, but are not limited to, amino, methylamino, dimethylamino, and methylethylamino.

The term "($NR_gR_j$)alkyl", as used herein, means a —$NR_gR_j$ group, as defined herein, appended to the parent molecular moiety through an alkyl group, as defined herein. Representative examples of ($NR_gR_j$)alkyl include, but are not limited to, (amino)methyl, (dimethylamino)methyl, and (ethylamino)methyl.

The term "($NR_gR_j$)alkoxy", as used herein, means a —$NR_gR_j$ group, as defined herein, appended to the parent molecular moiety through an alkoxy group, as defined herein. Representative examples of ($NR_gR_j$)alkoxy include, but are not limited to, (amino)methoxy, (dimethylamino)methoxy, and (diethylamino)ethoxy.

The term "($NR_gR_j$)carbonyl", as used herein, means a —$NR_gR_j$ group, as defined herein, appended to the parent molecular moiety through a carbonyl group, as defined herein. Representative examples of ($NR_gR_j$)carbonyl include, but are not limited to, aminocarbonyl, (methylamino)carbonyl, (dimethylamino)carbonyl, and (ethylmethylamino)carbonyl.

The term "($NR_gR_j$)sulfonyl", as used herein, means a —$NR_gR_j$ group, as defined herein, appended to the parent molecular moiety through a sulfonyl group, as defined herein. Representative examples of ($NR_gR_j$)sulfonyl include, but are not limited to, aminosulfonyl, (methylamino)sulfonyl, (dimethylamino)sulfonyl, and (ethylmethylamino)sulfonyl.

The term "sulfonyl", as used herein, means a —$S(O)_2$— group.

The term "thioalkoxy", as used herein, means an alkyl group, as defined herein, appended to the parent molecular moiety through a sulfur atom. Representative examples of thioalkoxy include, but are no limited to, methylthio, ethylthio, and propylthio.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable acid. Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, proprionic, hydrobromic, glucuronic, methanesulfonic, ethanesulfonic, naphthylene sulfonic, lactic, fumaric, oxalic, and succinic acid. Representative acid addition salts include, but are not limited to, ascorbic acid, (D)-tartaric acid, (L)-tartaric acid, phosphoric acid, salicylic acid, sulfuric acid, trifluoroacetic acid, and hydrochloric acid.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Prodrugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "treating", "treatment" or "treated" refers to administering a compound to a subject with the purpose to cure, heal, alleviate, relieve, alter, remedy, ameliorate, or improve a pain condition, pain disorder or pain resulting from a medical condition or disorder.

The term "in need of treatment thereof" is broadly defined to mean a human or animal patient in need of a pain reliever or analgesic to diminish or control the feelings of pain associated with an acute or chronic medical condition or disorder.

The term "α7 nAChR ligand" as used herein means a compound that binds to and/or selectively modulates nAChR activity. Such compounds may be organic or inorganic compounds analogs or stereoisomers thereof, or other chemical or biological compounds, natural or synthesized. Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric $(\alpha 7)_5$ receptors and α7* receptors, which denote a nAChR containing at least one α7 subunit.

Compositions of the Invention

The invention also provides pharmaceutical compositions for treating or preventing pain conditions or disorders comprising administering a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, dissolving or suspending the drug in an oil vehicle can administer a parenterally administered drug form.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution.

In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of formula (I) administered to a human or lower animal may range from about 0.0003 to about 30 mg/kg of body weight. For purposes of oral administration, more preferable doses can be in the range of from about 0.001 to about 0.1 mg/kg body weight. If desired, the effective daily dose can be divided into multiple doses for purposes of administration; consequently, single dose compositions may contain such amounts or submultiples thereof to make up the daily dose.

It is understood that the effective daily dose will be decided by the attending physician within the scope of sound medical judgment. The specific therapeutically effective dose level for any particular patient will depend upon a variety of factors including the pain disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts.

EXAMPLES

Animals

Adult male Sprague-Dawley rats (250-300 g body weight, Charles River Laboratories, Portage, Mich.) were used, unless otherwise indicated. Animal handling and experimental protocols were approved by the Institutional Animal Care and Use Committee (IACUC) at Abbott Laboratories. Food and water were available ad libitum at all times except during testing. Food and water were available ad libitum at all times except during testing. All testing was done following procedures outlined in protocols approved by Abbott Laboratories' Institutional Animal Care and Use Committee.

For all surgical procedures, animals were maintained under isoflurane anesthesia (4-5% to induce, 1-3% to maintain), and the incision sites were sterilized using a 10% povidone-iodine solution prior to and after surgeries.

Example 1

Monoiodoacetate-Induced Osteoarthritis (MIA-OA) Model

Pain behavior was assessed by measurement of hind limb grip force (GF) in adult osteoarthritic rats. Unilateral knee joint osteoarthritis was induced in rats by a single intraarticular (i.a.) injection of sodium monoiodoacetate (MIA) (Sigma, St. Louis, Mo.) (3 mg in 0.05 ml sterile isotonic saline) into the joint cavity using a 26 G needle under light (2-4%) isoflurane anesthesia, as previously described (Chandran, P., Pai, M., Blomme, E. A., Hsieh, G. C., Decker, M. W., Honore, P., 2009, Pharmacological modulation of movement-evoked pain in a rat model, Eur. J. Pharmacol., 613, 39-45). Following injection, the animals were allowed to recover from the effects of anesthesia (usually 5-10 minutes) before returning them to their home cages.

Grip strength was assessed in osteoarthritic rats as a measure of activity-induced pain. Measurements of peak hind limb grip force were conducted by recording the maximum compressive force ($CF_{max}$), in grams of force, exerted on the hind limb strain gauge, in a commercially available grip force measurement system (Columbus Instruments, Columbus, Ohio). During testing, each rat was gently restrained and allowed to grasp the wire mesh frame (10×12 cm) attached to the strain gauge. The animal was then moved in a rostral-to-caudal direction until the grip was broken. Each rat was sequentially tested twice at an approximately two-three minute interval to obtain a raw mean grip force ($CF_{max}$ in gram force units). In order to account for the body weight differences among the rats, this raw mean grip force was converted to a maximum hind limb compressive force for each animal by dividing the $CF_{max}$ by the body weight of the rat in kg [($CF_{max}$ in gram force)/kg body weight].

After approximately 21 days, 5-(5-((1R,3r,5S)-8-azabicyclo[3.2.1]octan-3-yloxy)pyridine-2-yl)-1H-indole, referred to herein as Compound A, was administered. Compound A was administered in 10% DMSO/HBC vehicle orally at a volume of 2 ml/kg, 60 minutes before testing. The NSAID diclofenac (30 mg/kg, p.o.) was given 60 minutes before data collection and used as a positive control.

A group of age-matched naïve (not injected with MIA) animals was added as a comparator to the drug-dosed groups. The vehicle control response for each group of MIA-treated animals was defined as the 0% response (0% effect), whereas the naïve control group was defined as the normal response and as 100% effect. The % effects for each dose group was expressed as % return of response to normalcy, compared to the naïve group. That is, the % effect=(Treatment $CF_{max}$-Vehicle $CF_{max}$)/Vehicle $CF_{max}$)×100). Higher % effect numbers indicate increased relief from the pain in the model, with 100% indicating a return to the level of response seen in normal (non-osteoarthritic) animals.

The data obtained from various dose groups for the test compound were compared with data from the naïve group.

Figure 1:
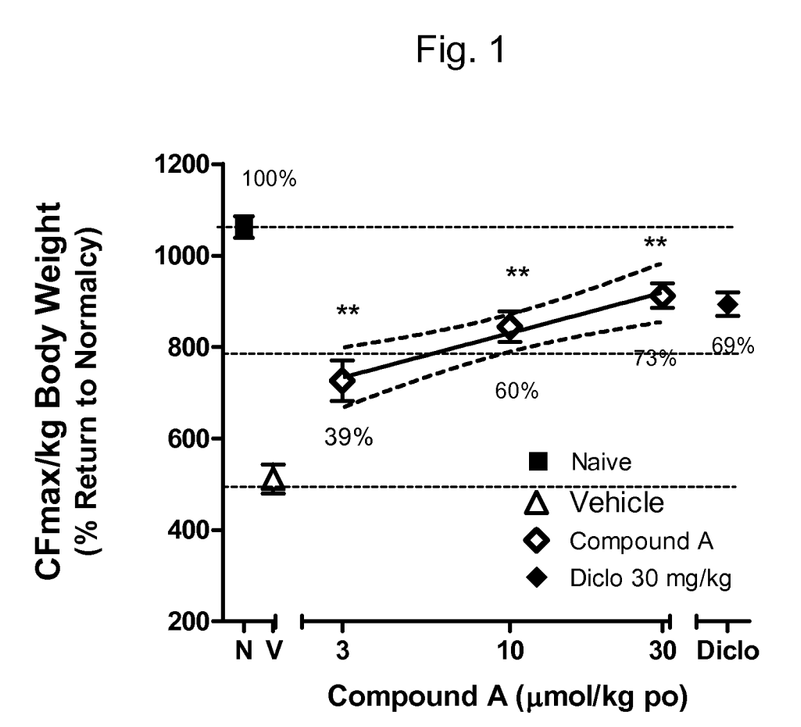
FIG. 1 graphically represents the effects of Compound A in a MIA-induced osteoarthritis pain model.

The test results are presented in FIG. 1. Representing the raw data as a percent return of grip force to normalcy, Compound A at 3, 10, and 30 μmol/kg demonstrated percent return of grip force to normalcy of approximately 39%, 60%, and 73%, respectively. $ED_{50}$ is approximately 6 μmol/kg. Note that diclofenac (30 mg/kg) is active as a positive control in this test, with a % Effect of about 69%. (FIG. 1, Doses given in μmol/kg, p.o., 60 minutes before data collection, diclofenac 30 mg/kg was p.o., given 60 minutes before data collection as positive control. Data are shown as mean grip force ($CF_{max}$/kg body weight)±standard error of the mean for n=6 per group. Diclofenac 30 mg/kg p.o. was utilized as positive control. Potential differences in grip force were evaluated by applying a one-way analysis of variance. Significance was assessed by post hoc analysis using Bonferroni's Multiple Comparison Test vs. vehicle group (*p<0.05, **p<0.01, compared to vehicle group)).

Compound A showed a statistically significant change in hind limb grip force strength versus a saline vehicle at less than about 100 micromoles/kg, for example, at less than about 30 micromoles/kg, in the MIA model of osteoarthritic pain following a single dose administration. Results indicate that the compounds of formula (I) are efficacious in an in vivo model of monoiodoacetate-induced osteoarthritis pain, and are active in the model at doses of ranging from about 3 to about 30 micromoles/kg of body weight.

Example 2

Chronic Constriction Injury (CCI) Model of Neuropathic Pain (Bennett Model)

Compound A demonstrates efficacy in a chronic constriction injury-induced (CCI) model of neuropathic pain. In particular, neuropathic pain was produced by following the method of Bennett and Xie (1988, Pain, 33, 87-107). The right common sciatic nerve was isolated at mid-thigh level, and loosely ligated by 4 chromic gut (4-0) ties separated by an interval of 1 mm. Sham rats underwent the same procedure, but without sciatic nerve constriction. All animals were allowed to recover for at least 2 weeks and no more than 5 weeks prior to testing of mechanical allodynia.

Tactile (mechanical) allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53,55. Rats were placed into inverted individual plastic containers (20×12.5×20 cm) on top of a suspended wire mesh grid, and acclimated to the test chambers for 20 min. The von Frey filaments were presented perpendicularly to the plantar surface of the selected hind paw, and then held in this position for approximately 8 seconds with enough force to cause a slight bend in the filament. Positive responses included an abrupt withdrawal of the hind paw from the stimulus, or flinching behavior immediately following removal of the stimulus.

A 50% paw withdrawal threshold ($PWT_{von\ Frey}$) was determined using an up-down procedure (Dixon, W. J., 1980, Efficient analysis of experimental observations, Ann. Rev. Pharmacol. Toxicol., 20, 441). To accomplish this, a series of calibrated von Frey filaments were tested covering a range from 0.25 g to 15 g. A withdrawal threshold of 0.25 g was assigned to animals that responded to all of the stimuli presented and a threshold of 15 g was assigned to rats that did not respond to any of the stimuli presented. An antiallodynic response was defined as a significant increase in the 50% threshold compared to saline treatment. Prior to the start of drug studies, baseline scores were determined for all animals. Only rats with a $PWT_{von\ Frey} \leq 5.0$ g were considered allodynic and utilized to test the analgesic activity of Compound A.

Compound A was administered at about 3, 10 and 30 μmol/kg in vehicle 30% 2-hydroxypropyl-beta-cyclodextrin (HBC) 2.0 ml/kg p.o. Gabapentin (500 μmol/kg in water 2.0 ml/kg p.o.) was used as positive control.

Figure 2:
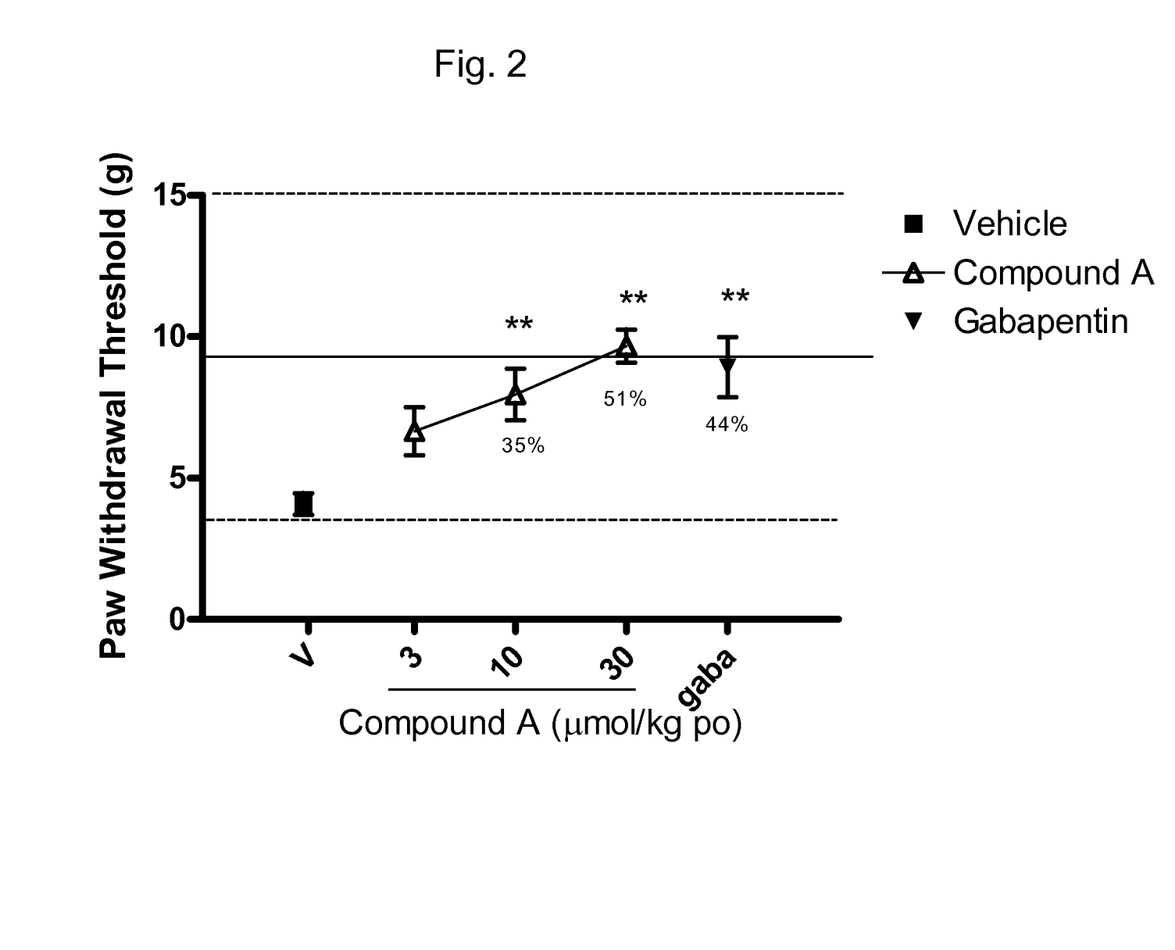
FIG. 2 graphically represents the effects of Compound A in a Chronic Constriction Injury (CCI) Model of Sciatic Nerve-Induced Neuropathic Pain.

Results are shown in FIG. 2. Compound A showed a statistically significant change in Paw Withdrawal Threshold versus a saline vehicle at less than about 100 micromoles/kg, for example, at less than about 30 micromoles/kg, in the CCI model of neuropathic pain following a single dose administration, which indicate that the compounds of formula (I) are effective analgesic agents for neuropathic pain at doses of ranging about 3 to about 30 micromoles/kg of body weight.

The above Examples are for illustrative purposes only and are not intended to limit the scope of the invention.

What is claimed is:

1. A method for treating osteoarthritis pain in a patient comprising:
administering a therapeutically effective amount of an α7 nAChR ligand to the patient, wherein the α7 nAChR ligand is a compound of formula (I), (I)

or a pharmaceutically acceptable salt, ester, or amide thereof, wherein
n is 2;
A is N;
R is hydrogen or alkyl;
L is selected from the group consisting of O and —N($R_a$)—;
$Ar^1$ is pyridinyl;
$Ar^2$ is (i)

wherein $Z_1$, $Z_2$, $Z_3$ and $Z_4$ are each carbon;
$R_b$ is selected from the group consisting of hydrogen and alkyl;

R₆ is selected from the group consisting of hydrogen, alkyl, and haloalkyl;

R₇ is hydrogen; and

R$_a$ is hydrogen.

2. The method of claim 1, wherein the α7 nAChR ligand is selected from the group consisting of:

- 5-{5-[(endo)-8-methyl-8-aza-bicyclo[3.2.1]oct-3-yloxy]-pyridin-2-yl}-1H-indole;
- 5-{5-[(exo)-8-methyl-8-aza-bicyclo[3.2.1]oct-3-yloxy]-pyridin-2-yl}-1H-indole;
- 5-{5-[(exo)-8-methyl-8-aza-bicyclo[3.2.1]oct-3-yloxy]-pyridin-2-yl}-2-trifluoromethyl-1H-indole;
- 4-{5-[(exo)-8-methyl-8-aza-bicyclo[3.2.1]oct-3-yloxy]-pyridin-2-yl}-1H-indole;
- 5-{6-[(endo)-8-methyl-8-aza-bicyclo[3.2.1]oct-3-yloxy]-pyridin-3-yl}-1H-indole;
- 5-{6-[(exo)-8-methyl-8-aza-bicyclo[3.2.1]oct-3-yloxy]-pyridin-3-yl}-1H-indole;
- [6-(1H-indol-5-yl)-pyridin-3-yl]-[(endo)-8-methyl-8-aza-bicyclo[3.2.1]oct-3-yl]-amine;
- [(endo)-8-methyl-8-aza-bicyclo[3.2.1]oct-3-yl]-[6-(2-trifluoromethyl-1H-indol-5-yl)-pyridin-3-yl]-amine;
- [6-(1H-indol-4-yl)-pyridin-3-yl]-[(endo)-8-methyl-8-aza-bicyclo[3.2.1]oct-3-yl]-amine;
- [(endo)-8-aza-bicyclo[3.2.1]oct-3-yl]-[6-(1H-indol-5-yl)-pyridin-3-yl]-amine;
- [6-(1H-indol-6-yl)-pyridin-3-yl]-[(endo)-8-methyl-8-aza-bicyclo[3.2.1]oct-3-yl]-amine;
- 5-{5-[(exo)-8-methyl-8-aza-bicyclo[3.2.1]oct-3-yloxy]-pyridin-3-yl}-1H-indole;
- (endo)-N-(5-(1H-Indol-5-yl) pyridin-3-yl)-8-methyl-8-azabicyclo[3.2.1]octan-3-amine;
- (endo)-N-(5-(1H-Indol-4-yl) pyridin-3-yl)-8-methyl-8-azabicyclo[3.2.1]octan-3-amine;
- (endo)-N-(5-(1H-Indol-6-yl) pyridin-3-yl)-8-methyl-8-azabicyclo[3.2.1]octan-3-amine;
- (endo)-N-{5-[2-(trifluoromethyl)-1H-indol-5-yl]pyridin-3-yl}-8-Methyl-8-azabicyclo[3.2.1]octan-3-amine;
- 5-{5-[(endo)-8-Azabicyclo[3.2.1]octan-3-yloxy]pyridin-2-yl}-1H-indole;
- (1R,3r,5S,8s)-3-(6-(1H-Indol-5-yl)pyridin-3-yloxy)-8-methyl-8-azabicyclo[3.2.1]octane 8-oxide;
- (1R,3r,5S,8r)-3-(6-(1H-Indol-5-yl)pyridin-3-yloxy)-8-methyl-8-azabicyclo[3.2.1]octane 8-oxide;
- 4-{5-[(endo)-8-Azabicyclo[3.2.1]octan-3-yloxy]pyridin-2-yl}-1H-indole; and
- 5-{5-[(exo)-8-Azabicyclo[3.2.1]octan-3-yloxy]pyridin-2-yl}-1H-indole.

3. The method of claim 1, further comprising:

administering an effective amount of at least one of a non-steroid anti-inflammatory agent, an opioid, a tricyclic antidepressant and an anticonvulsant in combination with the neuronal nicotinic acetylcholine receptor ligand.

4. A method for treating osteoarthritis pain in a patient, the method comprising administering a therapeutically effective amount of an α7 nAChR ligand selected from:

- 5-{5-[(endo)-8-Azabicyclo[3.2.1]octan-3-yloxy]pyridin-2-yl}-1H-indole;
- 4-{5-[(endo)-8-Azabicyclo[3.2.1]octan-3-yloxy]pyridin-2-yl}-1H-indole;
- 5-{5-[(exo)-8-Azabicyclo[3.2.1]octan-3-yloxy]pyridin-2-yl}-1H-indole;
- 4-{5-[(exo)-8-methyl-8-aza-bicyclo[3.2.1]oct-3-yloxy]-pyridin-2-yl}-1H-indole; and
- 5-{6-[(endo)-8-methyl-8-aza-bicyclo[3.2.1]oct-3-yloxy]-pyridin-3-yl}-1H-indole, or a pharmaceutically acceptable salt, solvate, ester or amide thereof.

* * * * *